US006528150B2

(12) United States Patent
Nazarova et al.

(10) Patent No.: US 6,528,150 B2
(45) Date of Patent: Mar. 4, 2003

(54) COATING GRADIENT FOR LUBRICIOUS COATINGS ON BALLOON CATHETERS

(75) Inventors: Irina Nazarova, Woodbury, MN (US); Lixiao Wang, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 59 days.

(21) Appl. No.: 09/827,284

(22) Filed: Apr. 5, 2001

(65) Prior Publication Data

US 2001/0019762 A1 Sep. 6, 2001

Related U.S. Application Data

(63) Continuation of application No. 09/764,180, filed on Jan. 17, 2001, now Pat. No. 6,261,630, which is a continuation of application No. 09/306,939, filed on May 7, 1999, now Pat. No. 6,221,467, which is a continuation-in-part of application No. 08/868,301, filed on Jun. 3, 1997, now Pat. No. 5,902,631.

(51) Int. Cl.[7] .................. A61M 25/02; A61M 25/10
(52) U.S. Cl. .................. 428/212; 428/213; 604/265
(58) Field of Search .................. 604/265; 428/213, 428/212

(56) References Cited

U.S. PATENT DOCUMENTS

| 2,814,296 A | 11/1957 | Everett ................. 128/339 |
| 3,566,874 A | 3/1971 | Shepherd ................ 128/349 |
| 3,826,674 A | 7/1974 | Schwarz ................. 117/62.2 |
| 4,026,296 A | 5/1977 | Stoy et al. .............. 128/349 |
| 4,100,309 A | 7/1978 | Micklus et al. ............ 427/2 |
| 4,156,066 A | 5/1979 | Gould .................... 528/73 |
| 4,156,067 A | 5/1979 | Gould .................... 528/73 |
| 4,248,685 A | 2/1981 | Beede et al. .......... 204/159.22 |
| 4,373,009 A | 2/1983 | Winn ................... 428/424.2 |
| 4,447,590 A | 5/1984 | Szycher ................. 528/76 |
| 4,459,317 A | 7/1984 | Lambert ................. 427/2 |
| 4,459,318 A | 7/1984 | Hyans ................... 427/36 |
| 4,467,073 A | 8/1984 | Creasy ................. 525/127 |
| 4,490,421 A | 12/1984 | Levy ..................... 428/35 |
| 4,588,398 A | 5/1986 | Daugherty et al. ........ 604/265 |

(List continued on next page.)

FOREIGN PATENT DOCUMENTS

| EP | 0 380 102 | 8/1990 | .......... A61M/29/02 |
| EP | 0 480 809 A2 | 4/1992 | |
| EP | 0 519 604 A2 | 12/1992 | |
| EP | 0 592 870 A1 | 4/1994 | |
| EP | 0 693 293 | 1/1996 | |
| WO | 91/08790 | 6/1991 | .......... A61M/25/00 |
| WO | 94/27665 | 12/1994 | |
| WO | 98/55172 | 12/1998 | |

OTHER PUBLICATIONS

Gantrez® AN Copolymer pp, 1–13; 1995.
M. Szycher, "Blood Compatible Materials and Devices Perspectives Towards the 21st Century", C.P. Sharma and M. Szycher eds., 1991.
Graham, Neil B., "Poly(ethylene oxide) and Related Hydrogels", *Hydrogels in Medicine and Pharmacy*, vol. II Polymers, Ed. by N.A. Peppas, CRC Press, Inc., Boca Raton Florida, 1986, pp. 95–113.

*Primary Examiner*—Caixia Lu
(74) *Attorney, Agent, or Firm*—Vidas, Arrett & Steinkraus P.A.

(57) ABSTRACT

This invention relates to a dilatation balloon formed from an extruded tubular preform by blowing, said balloon having a body, at least one cone and at least one waist portion wherein said balloon has a lubricity coating gradient from the body portion which has the lowest coat thickness to the waist portion which has the highest coat thickness said coating applied to said extruded tubular preform prior to forming said balloon by blowing.

17 Claims, 1 Drawing Sheet

U.S. PATENT DOCUMENTS

| | | | |
|---|---|---|---|
| 4,705,709 A | 11/1987 | Vailancourt | 428/36 |
| 4,863,424 A | 9/1989 | Blake, III et al. | 604/54 |
| 4,876,126 A | 10/1989 | Takemura et al. | 428/35.7 |
| 4,921,483 A | 5/1990 | Wijay et al. | 604/96 |
| 4,977,901 A | 12/1990 | Ofstead | 128/772 |
| 4,990,357 A | 2/1991 | Karakelle et al. | 427/2 |
| 5,026,607 A | 6/1991 | Kiezulas | 428/423.7 |
| 5,041,100 A | 8/1991 | Rowland et al. | 604/265 |
| 5,077,352 A | 12/1991 | Elton | 525/409 |
| 5,084,315 A | 1/1992 | Karimi et al. | 428/36.6 |
| 5,091,205 A | 2/1992 | Fan | 427/2 |
| 5,100,381 A | 3/1992 | Burns | 604/96 |
| 5,135,516 A | 8/1992 | Sahatjian et al. | 604/265 |
| 5,229,211 A | 7/1993 | Murayama et al. | 428/424.4 |
| 5,348,538 A | 9/1994 | Wang et al. | 604/96 |
| 5,441,488 A | 8/1995 | Shimura | 604/265 |
| 5,490,839 A | 2/1996 | Wang et al. | 604/96 |
| 5,503,631 A | 4/1996 | Onishi et al. | 604/96 |
| 5,509,899 A | 4/1996 | Fan et al. | 604/96 |
| 5,531,715 A | 7/1996 | Engelson et al. | 604/265 |
| 5,556,383 A | 9/1996 | Wang et al. | 604/96 |
| 5,587,125 A | 12/1996 | Roychowdhury | 264/515 |
| 5,670,558 A | 9/1997 | Onishi et al. | 523/112 |
| 5,693,034 A | 12/1997 | Buscemi et al. | 604/265 |
| 5,749,837 A | 5/1998 | Palermo et al. | 600/585 |
| 5,792,415 A | 8/1998 | Hijlkema | 264/530 |
| 5,826,588 A | 10/1998 | Forman | 128/898 |
| 5,849,209 A | 12/1998 | Kindt-Larsen et al. | 249/134 |
| 6,046,143 A | 4/2000 | Khan et al. | 508/208 |
| 6,071,266 A | 6/2000 | Kelley | 604/265 |

COATING GRADIENT FOR LUBRICIOUS COATINGS ON BALLOON CATHETERS

CROSS REFERENCE TO RELATED U.S. APPLICATIONS

This application is a Continuation of application Ser. No. 09/764,180, now U.S. Pat. No. 6,261,630, filed Jan. 17, 2001, which is a Continuation application Ser. No. 09/306,939, now U.S. Pat. No. 6,221,467, filed May 7, 1999 which is a Continuation-In-Part of application Ser. No. 08/868,301 filed Jun. 3, 1997 now U.S. Pat. No. 5,902,631.

FIELD OF THE INVENTION

This invention relates to medical devices which have a segment which is inserted into the body and a segment which is retained outside the body for manipulation. In particular, it relates to structures for which the in-the-body portion is a dilation balloon coated with a lubricious compound. Specifically, this invention relates to a method of coating a balloon which creates lubricity gradients on the balloon. The balloon is coated prior to being blown and the resultant balloon has different amounts of coating on the different parts of the balloon.

BACKGROUND OF THE INVENTION

Dilatation catheters are devices which have an inflatable balloon at the distal end and are utilized in medical procedures such as angioplasty to eliminate stenoses or blockages. The balloons are inserted into vessels in the body to open stenoses or blockages in the vascular system, usually by means of a catheter having a balloon at its distal end. To this end, the catheters may be inserted into a blood vessel, advanced through the blood vessel to a target site (i.e. the location of the stenosis or blockage) and the balloon is then inflated by supplying a liquid such as a radiopaque substance for angiography, through an inflation lumen. The inflation of the balloon causes stretching and expansion of the target site, i.e. a blood vessel, in order to eliminate the stenosis or blockage thereby reestablishing acceptable blood flow.

There are various types of catheters having single or multiple lumen, and some which are over-the-wire and some which are not. For the purpose of the present invention, all catheters will hereinafter be referred to as "balloon catheters."

These devices need a certain degree of lubricity so as to avoid injury to tissues, mucous membranes and other bodily parts with which they come into contact during insertion into a blood vessel, for instance. Balloons are typically made of polymeric materials including nylon, Selar®, polyether-polyester block copolymers (e.g. Hytrel® or Amitel®), poly(amide-ether-ester) block copolymers such as Pebax®D, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof. Such materials are typically inherently non-lubricious making it necessary to add some type of lubricious coating to the surface in order to advance the device through the blood vessel more easily.

However, once the balloon is at the target site, it will be necessary that it may be retained easily at the site during expansion or contraction without slippage. This is more readily accomplished when the balloon material has no lubricity.

Balloons will therefore typically have a lubricating portion and a non-lubricating portion to avoid what is referred to in the industry as the "watermelon seed" problem wherein a balloon which is too lubricious shoots forward on inflation causing accidental slippage from the target site. U.S. Pat. No. 5,503,631 to Onishi et al. discloses a vasodilating catheter balloon whose body has a lubricating portion and a non-lubricating portion. The lubricious property of the balloon is created by grafting a lubricious coating onto a non-lubricious substrate. Only the tapered portions on opposite ends of the balloon were treated.

The present inventors have now found a simplistic method for coating a balloon prior to formation of the balloon which achieves a lubricious coating gradient necessary for the successful use of a balloon catheter. The balloon exhibits superior retention at the target site without the "watermelon seed" effect, and exhibits excellent lubricity during insertion into the body cavity.

SUMMARY OF THE INVENTION

The present invention relates to a dilatation balloon formed from an extruded tubing by blowing. The balloon has a body, at least one cone and at least one waist portion and a lubricity coating gradient from the body portion which has the lowest coating thickness to the waist portion which has the highest coating thickness. The balloon material is first extruded into a tubular form prior to balloon formation which is accomplished by dry blowing the balloon material. The lubricious coating is applied to the extruded tubing prior to blowing the balloon. It is the different amounts of expansion which occur for the body, the cone and the waist which cause the lubricity gradient.

DETAILED DESCRIPTION OF THE PREFERRED EMBODIMENTS

Figure 1:
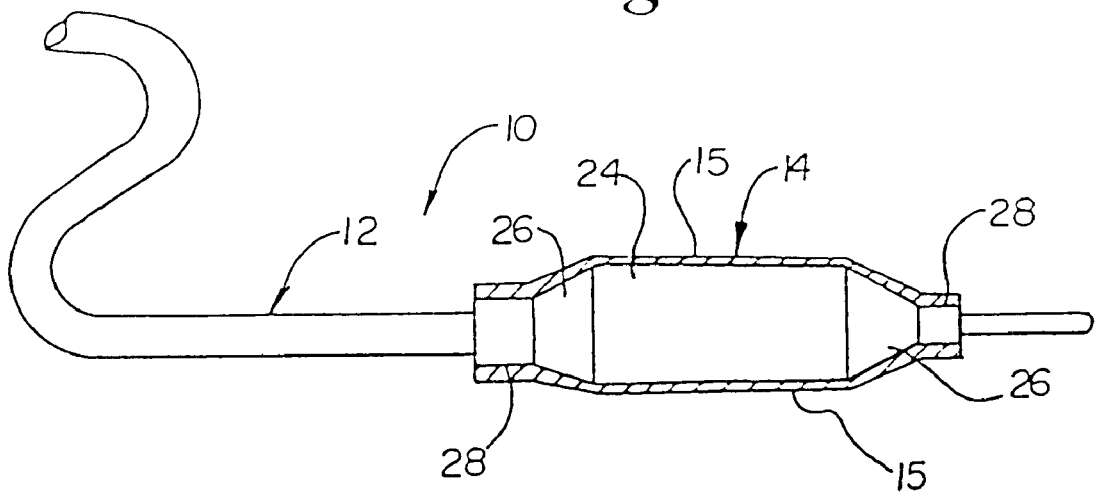
FIG. 1 is a perspective view of a dilatation catheter that includes an inflated coated balloon of the present invention.

A dilatation balloon catheter of the present invention, illustrated generally at 10 in FIG. 1, includes an inflatable balloon 14 mounted at the distal end of an elongated flexible shaft 12. Except as noted herein, catheter 10 is conventional in its construction, providing a lumen communicating with the interior of the balloon 14, for inflation and deflation of the balloon, and other optional features conventional in the dilatation catheter art. The balloon 10, has an inflated configuration, illustrated in FIG. 1 and is made up of three main portions: the body 14, the cones 26 and the waist portions 28. FIG. 1 illustrates the coating gradient wherein the coating 15 on body 14 is at a lower coating thickness than the coating on cones 26 which is at a lower coating thickness than the coating on the waist portions 28, thereby establishing a coating gradient.

Figure 2:
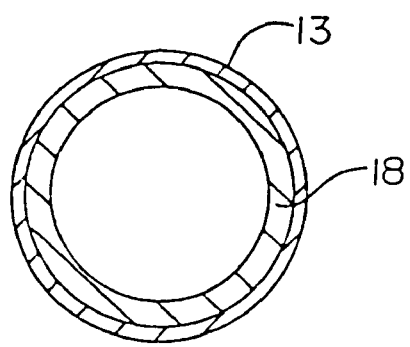
FIG. 2 is a cross sectional view of the tubing prior to blowing the balloon.

FIG. 2 represents a cross-sectional view of the extruded tubing from which the balloon is blown. The tubing comprises a wall 16 such as formed from Pebax® and a coating 13 disposed thereon.

The present invention involves a process for the coating of dilatation balloons which creates a gradient coating on the balloons, the body of the balloon having less of the lubricious coating than the cones which have less coating than the waist.

Balloons are typically made of thermoplastic polymeric materials including general classes such as thermoplastic elastomers, i.e. block copolymers; homopolymers, copolymers and terpolymers of ethylene; homopolymers, copolymers and terpolymers of propylene; ethylene α-olefins; polyesters; polyamides; polyurethanes; polycarbonates, vinyl copolymers; ionomer materials and so forth. More specifically, materials such as nylon, Selar®, polyetherpolyester block copolymers (i.e. Hytrel®), Pebax® (polyether block amide copolymers), Surlyn®, polyethylene terephthalate, polytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters or other similar extrudable thermoplastic, polymeric materials, or composites thereof may be utilized in the present invention. Thermosetting materials such as polyimides may also be utilized.

Balloon materials which are preferable to the present invention include polyether block amides, such as Pebax® 7033 or 7233; polyester block ethers such as Arnitel® EM 40; polyethylene terephthalate; and nylon. The formation of catheter balloons made of block copolymer elastomers where the hard segments are polyester or polyamide and the soft segments are polyether, is discussed in U.S. Pat. No. 5,556,383 issued Sep. 17, 1996 to Wang et al. incorporated by reference herein.

Balloon formation may be carried out in any conventional manner with conventional extrusion and blowing techniques, but basically there are three major steps in the process which include extruding a tubular preform, blow molding the balloon and annealing the balloon. Depending on the balloon material employed, the preform may be axially stretched before it is blown. Techniques for balloon formation are discussed in U.S. Pat. No. 4,490,421 to Levy and in U.S. Pat. No. 5,348,538 issued Sep. 20, 1994 to Wang et al.

The present invention involves applying the lubricity coatings to the balloon material when it is in the tubular form, prior to blowing the balloon. The coating is applied to the entire tube at a constant and consistent coating thickness. If the balloon material is stretched, the coating may be applied before or after the stretching.

The lubricity gradient is created by expansion of the various parts of a balloon to different sizes. The body of the balloon expands the most while the waist expands only slightly if at all and the cones exhibit an intermediate expansion. The balloon body, for instance, may expand to 4–8 times the size of the tubular preform, while the waist may expand only slightly or remain about the same size, during balloon formation. The expansion of the body creates more surface area while the amount of coating remains the same thereby reducing the coating thickness per unit area on the body to a much greater degree than the reduction in coating thickness on either the body or the waist.

The present inventors have found that by applying the lubricious coating prior to balloon formation, the coating thickness on the body, which expands more, will be lower while the waist has a relatively higher coating thickness. The thickness on the cone varies inversely in accordance with the ratio of expansion along the length thereof. Since the coating thickness will vary in accordance with the same factors which affect wall thickness variability, the ratio of coating thickness to balloon wall material thickness will be approximately constant along the length of the balloon. In other words, the coating thickness on the balloon will be proportional to the thickness of the balloon wall after blowing. The thinner the balloon wall, the thinner the coating. The coating thickness after blowing, may be controlled by the thickness of the coating applied to the tubular form.

The present inventors have found that the lubricious coatings useful herein include any hydrophilic compound or any low friction hydrophobic coating which imparts lubricity to the balloon material. The method of the present invention for forming lubricity gradients on the balloon itself, is not dependent on the coating utilized. The lubricity gradient coating is a result of the method utilized to apply the coating rather than having any dependence on the type of coating utilized. Of course, some coatings are more desirable than others.

This lubricity gradient is desirable to prevent the "watermelon seed" effect. If the body of the balloon is too lubricious, the balloon may slip from the target site when the liquid used for balloon expansion is injected through the inflation lumen of the catheter, and into the balloon. It is critical to operations where balloon catheters are utilized, such as angioplasty, that the operator, usually the physician, is able to accurately and precisely position the balloon in the blocked vessel to create or expand the channel to restore acceptable levels of blood flowing through the vessel.

If the body of the balloon has an insufficient amount of lubricious coating, the introduction of the uninflated balloon into the body will be more difficult due to the higher friction between the balloon and the patient's tissue or blood vessels.

In contrast, for stent delivery, it may be desirable to have less lubrication on the balloon body than on the cones to prevent stent slippage from the target site.

The present method of coating catheter balloons has been found to produce balloons which are readily retained at target sites, yet have enough lubricity to be easily inserted into the vessels of patients without excessive discomfort.

Any hydrophobic or hydrophilic compound that imparts lubricity may be utilized in the coating method of the present invention. Examples of useful hydrophobic coatings include silicone lubricants or polymers and fluoropolymer coatings.

There are many hydrophilic compounds that may be utilized in the present invention. The water soluble lubricants useful herein include polyalkylene glycols, alkoxy polyalkylene glycols, homopolymers and copolymers of (meth) acrylic acid, copolymers of methylvinyl ether and maleic acid, poly(vinylpyrrolidone) homopolymers, copolymers of vinyl pyrrolidone, poly(N-alkylacrylamide), poly (vinyl alcohol), poly(ethyleneimine), polyamides, methyl cellulose, carboxymethylcellulose, polyvinylsulfonic acid, heparin, dextran, modified dextran, chondroitin sulphate and lecithin. The polymers are typically chain-structured, non-crosslinked and water soluble having a hydrophilic group such as —OH, —CONH$_2$, —COOH, —NH$_2$, —COO—, —SO$_3$, —NR$_3^+$ and so forth where R is alkyl or hydrogen.

Derivatives of these polymers may also be utilized providing, even if they are not water soluble, that they are still of a structure which is capable of being hydrated, or is dispersible in water. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above mentioned water soluble polymers. Also useful are polymers crosslinked with substances having more than one reactive functional group such as diazonium, azide isocyanate, acid chloride, acid anhydride, imino carbonate, amino, carboxyl, epoxy, hydroxyl and aldehyde groups. Further polymers include those copolymerized with vinyl, acrylic acid, methacrylic acid, diene compounds, and so forth.

The polyalkylene glycols or alkoxy polyalkylene glycols have the following general formula:

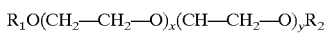

$R_1$ and $R_2$ may be the same or different and can be H or an alkyl group having 1 to about 6 carbon atoms, x is from 2 to about 500; and y is from 0 to about 100.

The polyalkylene glycols and alkoxy polyalkylene glycols may also contain functional groups such as, for example, hydroxyl, sulfur, nitrogen or oxygen.

Hydrophilic lubricants are beneficial because they will quickly swell in the blood stream.

In a preferred embodiment of the present invention, the hydrophilic coating is based on a maleic anhydride copolymer. Examples of such copolymers include poly(ethylene-maleic anhydride) sold by Aldrich Chemical Co. maleic anhydride-methyl vinyl ether copolymers such as Gantrez® AN 169 sold by G.A.F. Corporation. With such a coating material the lubricity may be altered by differential hydrolysis of the anhydride groups of the polymer and neutralization of the resulting acid groups. This may be readily accomplished by using a high pH solution (pH about 10 or higher, suitably 10–12) using a gradual drawing, successive dipping or other technique as described above.

Another way the maleic anhydride copolymer may be modified is by partial reaction with a solution containing an anhydride or carboxylic acid reactive compound such as an amine, alcohol, epoxy or imine compound. The reactive compound may suitably be a low molecular weight monofunctional compound, in which case hydrophilicity will usually be reduced. Polyfunctional compounds which produce surface crosslinking may also be employed. Polyethylene glycols or monohydroxy derivatives thereof may also be employed. Treatment of the coating with such reactive compounds may be combined with neutralization reactions of unreacted acid groups also obtained from the specific reactions or from hydrolysis of any unreacted anhydride groups remaining after such reactions.

Carboxylic acid-containing polymers may also be used as coating materials in the invention. Copolymers of acrylic acid, methacrylic acid, maleic acid, fumaric acid or other polymerizable ethylenically unsaturated acids are examples.

In another embodiment, a hydrogel coating is provided with a lubricity gradient. For example polyethylene oxide may be captured in an interpenetrating crosslinked acrylic polymer network by polymerizing a mixture of an acrylic monomer composition comprising a monomer having plural (meth)acrylate groups and polyethylene oxide, thereby providing a hydrogel coating.

In general hydrophilic lubricious coating materials are preferred as coating materials for use in the invention. However hydrophobic lubricious coating materials can be similarly provided with a gradient of lubricity and thus employed in the invention. Additional examples of preferable hydrophilic coating materials include the homopolymers and copolymers of vinyl pyrrolidone; polyacrylamides; polyethylene oxides; polyvinyl alcohols; (meth) acrylic acid homopolymers and copolymers; ionomeric polymers; collagen; polycarboxylic acids and so forth (which may optionally be mixed with polyurethane).

The coating compositions of the present invention may be coated out of a solvent or a cosolvent mixture using any conventional coating techniques such as dipping, spraying, brushing, and so forth. A preferable method for coating is dipping the tubular preform into the solution.

Useful solvents include alcohols, aliphatic hydrocarbons, aromatic hydrocarbons, chlorinated solvents, esters, glycols, glycol ethers, ketones, and so forth. Polar solvents include alcohols, glycols, water and so forth. Specific examples include ethanol, methanol, isopropanol, stearyl alcohol, ethylene glycol, propylene glycol, glycerin, water and so forth. Non-polar solvents include aliphatic hydrocarbons such as heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits and so forth.

For hydrophilic coatings, the preferable solvents are more polar and preferably include the alcohols such as isopropyl alcohol or isopropanol and water and mixtures thereof. A 1–20% solution of lubricious polymer is preferably utilized and more preferably a solution of about 3% to about 10 wt-% of the polymer is used.

The coating thickness, once the solvent has evaporated, is preferably from about 1 to about 10 $\mu$m, more preferably from about 2 to about 6 $\mu$m and most preferably from about 2 to about 4 $\mu$m. The solvent may be allowed to evaporate at ambient temperatures or the tubing may be dried.

The tubular preform may then be blown into a balloon using any standard blowing techniques. The coating thickness, after blowing, will vary from the lowest coating thickness on the body portion of the balloon, to higher coating thickness on the cones and even higher coating thickness on the waist. For instance, the thickness on the balloon body may be from about 0.2 $\mu$m to about 1 $\mu$m, preferably from about 0.3 $\mu$m to about 0.8 $\mu$m, while that on the cones or waist may be from about 1 $\mu$m to about 10 $\mu$m, preferably from about 2 $\mu$m to about 6 $\mu$m.

The coefficients of static friction vary depending on the coating thickness and will preferably be less on the cone and waist portions than on the body portion.

The preferable hydrophilic coating materials have been found to exhibit excellent adhesion to the balloon material.

The following non-limiting examples further illustrate the coating method of the present invention.

EXAMPLES

Example 1

Pebax® tubing segments of conventional dimension for a 3 mm angioplasty balloon were coated with a hydrophilic coating of a 10% solution of poly(ethylene maleic acid). The tubing segments were dried at 85° C. for 2 hrs. The coating thickness applied was 2–4 micrometers ($\mu$m).

The coated tubing segments were blown into a 3 mm balloon.

Coating thickness on the balloon body portion was 0.3–0.6 $\mu$m while on the cones it became thicker and on the waist it stayed nearly the same as the original dried coating thickness (2–4 microns). The coefficients of static friction on the balloons body portions were 0.141–0.168, whereas for waist portions they were 0.035–0.065.

Example 2

Pebax® tubing is coated with a hydrophilic coating of a 3–10% solution of polyvinylpyrrodlidone (PVP) in a mixed IPA/water (80/20 ratio) solvent. The tubing is dried at about 85° C. for 2 hrs to remove solvent. The coated tubing is blown into balloons at a temperature of about 95° C. The coating gives the balloons a different lubricity between the body and waist portions.

Example 3

Pebax tubing segments were coated with hydrophilic coating using a 5% solution of polyethylene oxide in a mixed IPA/water (80/20 ratio) solvent and a 5% solution of diacrylate monomers in IPA with a polymerization initiator. The tubing was dried at about 90° C. for 3 hours, or under UV-light for 45 seconds. The coated tubing was blown into balloons at about 95° C. The coating thickness on the balloon bodies was 0.15–0.30 microns, on cones it was about 1–2 microns.

Example 4

Pebax tubing segments were coated with hydrophilic coating of 3% solution of acrylamide in mixed IPA/water solvent. The coated tubing segments were dried at 90° C. for 3 hours and then blown into balloons. A large difference between the lubricity of the body and cones of the balloons was obtained.

Example 5

Balloons made of Pebax material are coated with a hydrophilic coating by spraying the body and cone portions for different time periods with a 3–5% solution of polyvinylpyrrolidone in IPA/water. The coated balloons are dried at 50° C. for 6 hours. The coating thickness varied on the body cones according to the different spray times used.

Example 6

Pebax tubing segments were coated of a 2% solution of silicon liquids, Dow Corning DC-360 and MDX-4 (relative weight ratio 2:1), in heptane. The coatings were dried at 50° C. and RH 50% for 4 hours. The coated tubing segments were blown into balloons at 95° C. The coating thickness and lubricity was different on the body and waist portions of the balloons.

Those skilled in the art may recognize other equivalents to the specific embodiments described herein which equivalents are intended to be encompassed by the claims attached hereto:

1. A dilatation balloon formed from an extruded tubular preform by blowing, said balloon having a body, at least one cone and at least one waist portion wherein said balloon has a lubricity coating on its surface with a gradient of thickness from the body portion which has the lowest coating thickness to the waist portion which has the highest coating thickness and wherein the surface has a gradient of lubricity.

2. The dilatation balloon of claim 1 wherein said lubricity coating is applied to said tubular preform before blowing.

3. The dilatation balloon of claim 1 wherein said lubricity coating comprises at least one copolymer of maleic acid.

4. The dilatation balloon of claim 3 wherein said copolymer of maleic acid is obtained from maleic anhydride copolymer modified by reaction of some of the anhydride groups thereof with a member selected from the group consisting of monofunctional amines, alcohols, epoxies, imines and mixtures thereof.

5. The dilatation balloon of claim 3 wherein said copolymer of maleic anhydride is selected from the group consisting of poly(ethylene-maleic anhydride) copolymer and maleic anhydride-methyl vinyl ether copolymer.

6. The dilatation balloon of claim 1 wherein said lubricity coating comprises a hydrogel polymer.

7. The dilatation balloon of claim 6 wherein said hydrogel polymer comprises polyethylene oxide captured in an interpenetrating crosslinked acrylic polymer network.

8. The dilatation balloon of claim 1 wherein said lubricity coating comprises at least one polycarboxylic acid.

9. The dilatation balloon of claim 1 wherein said lubricity coating comprises a (meth)acrylic acid homopolymer or copolymer.

10. The dilatation balloon of claim 1 wherein said lubricity coating comprises a vinyl pyrrolidone homopolymer or copolymer.

11. The dilatation balloon of claim 1 wherein said lubricity coating gradient is created by expansion of a segment of polymer tubing coated with a uniform coating of said lubricity coating so as to form said balloon with differently sized waist, cone and body portions.

12. The dilatation balloon of claim 11 wherein said coated tubing is dried at temperature of from about 50° C. to about 90° C. prior to said expansion.

13. The dilatation balloon of claim 11 wherein said lubricity coating is selected from the group consisting of hydrophobic polymers and hydrophilic polymers.

14. A catheter having mounted thereon a dilatation balloon of claim 11.

15. A medical device balloon having waist, cone and body portions, the balloon being coated with a lubricious coating, the lubricious coating having a thickness which varies such that the waist coating thickness is greater than the body coating thickness and wherein the surface has a gradient of lubricity.

16. A catheter having a balloon as in claim 1 mounted thereon.

17. A medical device balloon having a wall thickness which varies between different portions along the length thereof, the balloon characterized in that the coating thickness varies commensurately to the wall thickness such that the ratio of coating thickness to wall thickness is approximately constant and wherein the surface has a gradient of lubricity.

* * * * *